US012678167B2

(12) United States Patent
Tischler et al.

(10) Patent No.: US 12,678,167 B2
(45) Date of Patent: Jul. 14, 2026

(54) LEFT ATRIAL APPENDAGE CLOSURE IMPLANT

(71) Applicant: BOSTON SCIENTIFIC SCIMED, INC., Maple Grove, MN (US)

(72) Inventors: Brian Joseph Tischler, New Brighton, MN (US); Christopher J. Clark, St. Michael, MN (US); Dennis A. Peiffer, Brooklyn Park, MN (US); Thyna M. Chau, Oakdale, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 18/489,473

(22) Filed: Oct. 18, 2023

(65) Prior Publication Data

US 2024/0065698 A1 Feb. 29, 2024

Related U.S. Application Data

(63) Continuation of application No. 17/564,547, filed on Dec. 29, 2021, which is a continuation-in-part of
(Continued)

(51) Int. Cl.
*A61B 17/12* (2006.01)
*A61B 17/00* (2006.01)

(52) U.S. Cl.
CPC .... *A61B 17/12122* (2013.01); *A61B 17/0057* (2013.01); *A61B 17/12172* (2013.01);
(Continued)

(58) Field of Classification Search
CPC .......... A61B 17/0057; A61B 17/12122; A61B 17/12172; A61B 17/12131;
(Continued)

(56) References Cited

U.S. PATENT DOCUMENTS 5,375,612 A 12/1994 Cottenceau et al.
6,689,150 B1 * 2/2004 VanTassel .......... A61B 17/0057
604/500
(Continued)

FOREIGN PATENT DOCUMENTS

DE 10201200302 A1 10/2012
EP 2074953 A1 7/2009
(Continued)

OTHER PUBLICATIONS

Invitation To Pay Additional Fees and, Where Applicable, Protest Fee for International Application No. PCT/US2013/070091 dated Feb. 3, 2014.

*Primary Examiner* — Darwin P Erezo
*Assistant Examiner* — Christina C Lauer
(74) *Attorney, Agent, or Firm* — Seager, Tufte & Wickhem LLP

(57) ABSTRACT

A left atrial appendage closure implant may include a support frame including a first bend extending from a proximal collar to a second bend, a first segment extending from the second bend to a third bend, a second segment extending from the third bend to a fourth bend, and a third segment extending from the fourth bend to a distal collar, wherein the support frame is actuatable from a first constrained position to a second flowering position to a third mid-deployment position to a fourth unconstrained position. An implant may include a self-expanding support frame having a circumference and a central longitudinal axis, a membrane disposed over at least a portion of the support frame, and a plurality of anchors arranged into a first row and a second row such that the first row and the second row form a staggered pattern about the circumference of the support frame.

20 Claims, 17 Drawing Sheets

Related U.S. Application Data application No. 15/493,736, filed on Apr. 21, 2017, now Pat. No. 11,241,237, which is a continuation of application No. 14/057,573, filed on Oct. 18, 2013, now abandoned.

(60) Provisional application No. 61/726,337, filed on Nov. 14, 2012.

(52) U.S. Cl.
CPC .............. *A61B 2017/00526* (2013.01); *A61B 2017/00601* (2013.01); *A61B 2017/00632* (2013.01); *Y10T 29/49826* (2015.01)

(58) Field of Classification Search
CPC ...... A61B 2017/00632; A61B 17/1214; A61B 17/12145; A61B 17/12168
See application file for complete search history.

(56) References Cited

U.S. PATENT DOCUMENTS

| | | | |
|---|---|---|---|
| 7,972,359 | B2 | 7/2011 | Kreidler |
| 9,883,936 | B2 | 2/2018 | Sutton et al. |

| | | | | |
|---|---|---|---|---|
| 2001/0000797 | A1* | 5/2001 | Mazzocchi | A61B 17/12177 |
| | | | | 606/151 |
| 2002/0111647 | A1 | 8/2002 | Khairkhahan et al. | |
| 2005/0283186 | A1 | 12/2005 | Berrada et al. | |
| 2006/0052816 | A1 | 3/2006 | Bates et al. | |
| 2007/0066993 | A1* | 3/2007 | Kreidler | A61B 17/12122 |
| | | | | 606/213 |
| 2007/0162048 | A1 | 7/2007 | Quinn et al. | |
| 2008/0033475 | A1 | 2/2008 | Meng | |
| 2009/0099647 | A1* | 4/2009 | Glimsdale | A61B 17/12172 |
| | | | | 623/1.35 |
| 2011/0054515 | A1* | 3/2011 | Bridgeman | A61B 17/12122 |
| | | | | 606/200 |
| 2011/0301630 | A1 | 12/2011 | Hendriksen et al. | |
| 2012/0239083 | A1 | 9/2012 | Kreidler | |
| 2012/0283768 | A1* | 11/2012 | Cox | A61B 17/1219 |
| | | | | 606/198 |

FOREIGN PATENT DOCUMENTS

| | | |
|---|---|---|
| JP | 2009160402 A | 7/2009 |
| WO | 2005099365 A2 | 10/2005 |

* cited by examiner

LEFT ATRIAL APPENDAGE CLOSURE IMPLANT

CROSS-REFERENCE TO RELATED APPLICATIONS

This application is a continuation of U.S. application Ser. No. 17/564,547, filed Dec. 29, 2021, which is a continuation in part of U.S. application Ser. No. 15/493,736, filed Apr. 21, 2017, now U.S. Pat. No. 11,241,237, which is a continuation of U.S. application Ser. No. 14/057,573 filed Oct. 18, 2013, which claims priority to U.S. Provisional Ser. No. 61/726, 337 filed Nov. 14, 2012. All are hereby incorporated for reference.

TECHNICAL FIELD

The disclosure relates generally to percutaneous medical devices and more particularly to percutaneous medical devices for implantation into the left atrial appendage (LAA) of a heart.

BACKGROUND

Atrial fibrillation (AF) is the most common sustained cardiac arrhythmia, affecting over 5.5 million people worldwide. Atrial fibrillation is the irregular, chaotic beating of the upper chambers of the heart. Electrical impulses discharge so rapidly that the atrial muscle quivers, or fibrillates. Episodes of atrial fibrillation may last a few minutes or several days. The most serious consequence of atrial fibrillation is ischemic stroke. It has been estimated that up to 20% of all strokes are related to atrial fibrillation. Most atrial fibrillation patients, regardless of the severity of their symptoms or frequency of episodes, require treatment to reduce the risk of stroke. The left atrial appendage (LAA) is a small organ attached to the left atrium of the heart as a pouch-like extension. In patients suffering from atrial fibrillation, the left atrial appendage may not properly contract with the left atrium, causing stagnant blood to pool within its interior, which can lead to the undesirable formation of thrombi within the left atrial appendage. Thrombi forming in the left atrial appendage may break loose from this area and enter the blood stream. Thrombi that migrate through the blood vessels may eventually plug a smaller vessel downstream and thereby contribute to stroke or heart attack. Clinical studies have shown that the majority of blood clots in patients with atrial fibrillation are found in the left atrial appendage. As a treatment, medical devices have been developed which are positioned in the left atrial appendage and deployed to close off the ostium of the left atrial appendage. Over time, the exposed surface(s) spanning the ostium of the left atrial appendage becomes covered with tissue (a process called endothelization), effectively removing the left atrial appendage from the circulatory system and reducing or eliminating the amount of thrombi which may enter the blood stream from the left atrial appendage.

A continuing need exists for improved medical devices and methods to control thrombus formation within the left atrial appendage of patients suffering from atrial fibrillation.

SUMMARY

A medical device for left atrial appendage closure may include a delivery catheter having a lumen extending therethrough; and a left atrial appendage closure implant including a proximal collar, a distal collar, and a monolithic support frame extending therebetween, the support frame including: a first bend extending from the proximal collar to a second bend, a first segment extending from the second bend to a third bend, a second segment extending from the third bend to a fourth bend, and a third segment extending from the fourth bend to the distal collar, wherein the support frame is actuatable from a first constrained position to a second flowering position to a third mid-deployment position to a fourth unconstrained position.

A left atrial appendage closure implant may include a self-expanding support frame having a circumference and a central longitudinal axis, a membrane disposed over at least a portion of the support frame, and a plurality of anchors arranged into a first row and a second row such that the first row and the second row form a staggered pattern about the circumference of the support frame.

A method of manufacturing a left atrial appendage closure implant may include the steps of:

obtaining an elongate tubular member having a lumen extending therethrough and an annular ring member;

laser cutting the tubular member to form a proximal collar, a plurality of struts, a plurality of anchors interspersed among the plurality of struts, and a plurality of free distal ends;

forming the plurality of struts into a lattice of generally diamond-shaped wire portions;

fixedly attaching the plurality of free distal ends to the annular ring member;

positioning the plurality of struts such that a cross-sectional profile of the left atrial appendage closure implant in an unconstrained position includes a first bend extending radially outward from the proximal collar to a second bend, a first segment extending distally and radially inward from the second bend to a third bend, a second segment extending distally and radially inward from the third bend to a fourth bend, and a third segment extending proximally and radially inward from the fourth bend to the annular ring member; and attaching a membrane over at least a portion of the plurality of struts such that the plurality of anchors extends through the membrane.

Figure 1:
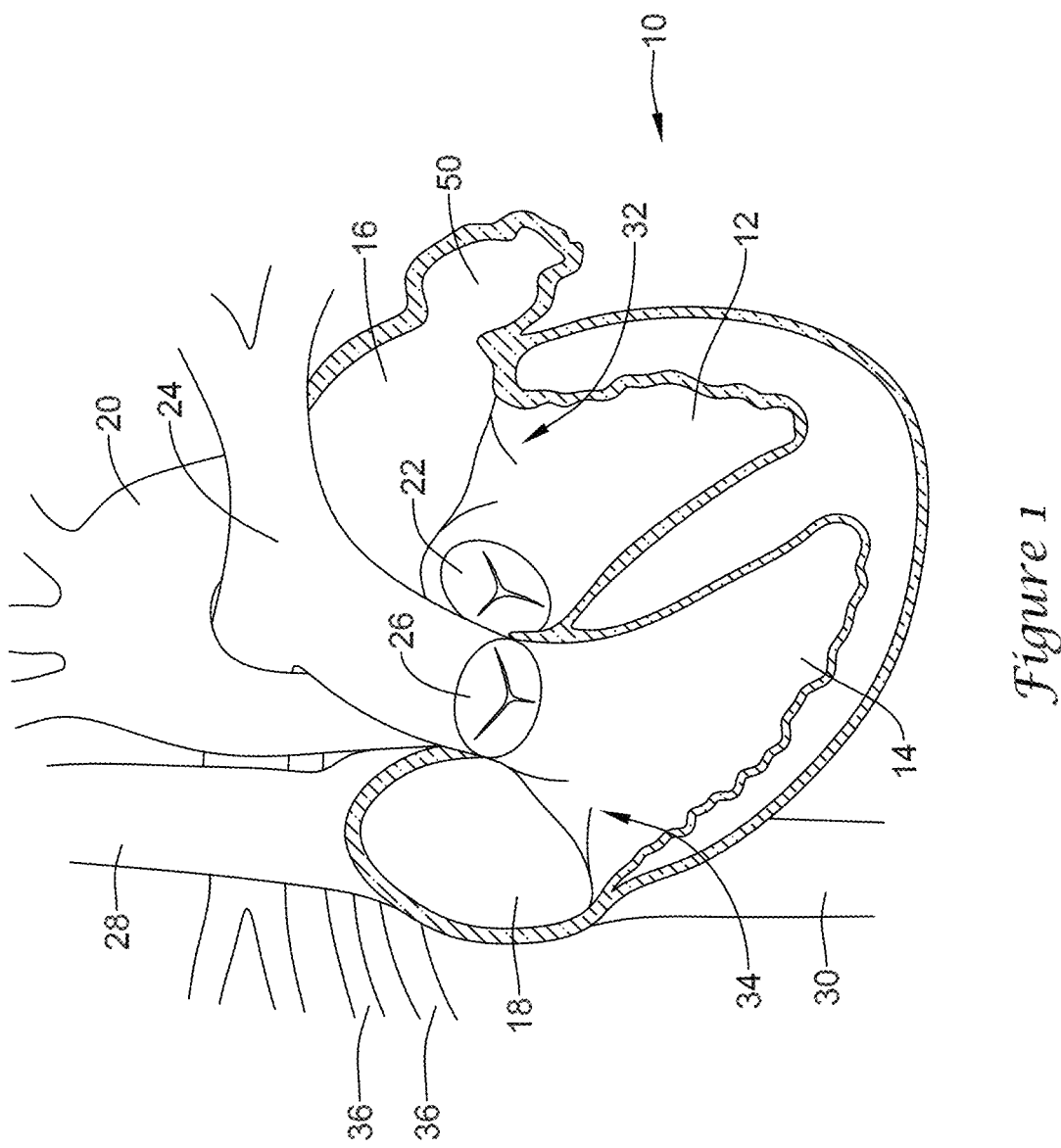
FIG. 1 is a schematic partial cross-sectional view of a heart.

While the invention is amenable to various modifications and alternative forms, specifics thereof have been shown by way of example in the drawings and will be described in greater detail below. It should be understood, however, that the intention is not to limit the invention to the particular embodiments described. On the contrary, the intention is to cover all modifications, equivalents, and alternatives falling within the spirit and scope of the invention.

DETAILED DESCRIPTION

For the following defined terms, these definitions shall be applied, unless a different definition is given in the claims or elsewhere in this specification.

The terms "upstream" and "downstream" refer to a position or location relative to the direction of blood flow through a particular element or location, such as a vessel (i.e., the aorta), a heart valve (i.e., the aortic valve), and the like.

The terms "proximal" and "distal" shall generally refer to the relative position, orientation, or direction of an element or action, from the perspective of a clinician using the medical device, relative to one another. While the terms are not meant to be limiting, "proximal" may generally be considered closer to the clinician or an exterior of a patient, and "distal" may generally be considered to be farther away from the clinician, along the length of the medical device.

The terms "monolithic" and "unitary" shall generally refer to an element or elements made from or consisting of a single structure or base unit/element. A monolithic and/or unitary element shall exclude structure and/or features made by assembling or otherwise joining multiple discrete elements together.

All numeric values are herein assumed to be modified by the term "about," whether or not explicitly indicated. The term "about", in the context of numeric values, generally refers to a range of numbers that one of skill in the art would consider equivalent to the recited value (i.e., having the same function or result). In many instances, the term "about" may include numbers that are rounded to the nearest significant figure. Other uses of the term "about" (i.e., in a context other than numeric values) may be assumed to have their ordinary and customary definition(s), as understood from and consistent with the context of the specification, unless otherwise specified.

Weight percent, percent by weight, wt %, wt-%, % by weight, and the like are synonyms that refer to the concentration of a substance as the weight of that substance divided by the weight of the composition and multiplied by 100.

The recitation of numerical ranges by endpoints includes all numbers within that range, including the endpoints (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following description should be read with reference to the drawings wherein like reference numerals indicate like elements throughout the several views. The detailed description and drawings are intended to illustrate but not limit the claimed invention. Those skilled in the art will recognize that the various elements described and/or shown may be arranged in various combinations and configurations without departing from the scope of the disclosure. The various individual elements described below, even if not explicitly shown in a particular combination, are nevertheless contemplated as being combinable or arrangable with each other to form other additional embodiments or to complement and/or enrich the described embodiment(s), as would be understood by one of ordinary skill in the art.

The occurrence of thrombi in the left atrial appendage (LAA) during atrial fibrillation may be due to stagnancy of the blood pool in the LAA. The blood may still be pulled out of the left atrium by the left ventricle, however less effectively due to the irregular contraction of the left atrium caused by atrial fibrillation. Therefore, instead of an active support of the blood flow by a contracting left atrium and left atrial appendage, filling of the left ventricle may depend primarily or solely on the suction effect created by the left ventricle. Further, the contraction of the left atrial appendage may not be in sync with the cycle of the left ventricle. For example, contraction of the left atrial appendage may be out of phase up to 180 degrees with the left ventricle, which may create significant resistance to the desired flow of blood. Further still, most left atrial appendage geometries are complex and highly variable, with large irregular surface areas and a narrow ostium or opening compared to the depth of the left atrial appendage. These aspects as well as others, taken individually or in various combinations, may lead to high flow resistance of blood out of the left atrial appendage.

In an effort to reduce the occurrence of thrombi formation within the left atrial appendage and prevent thrombi from entering the blood stream from within the left atrial appendage, a medical device has been developed that closes off the left atrial appendage from the heart and/or circulatory system, thereby lowering the risk of stroke due to thrombolytic material entering the blood stream from the left atrial appendage.

Turning to the drawings, FIG. 1 is a partial cross-sectional view of certain elements of a human heart 10 and some immediately adjacent blood vessels. A heart 10 may include a left ventricle 12, a right ventricle 14, a left atrium 16, and a right atrium 18. An aortic valve 22 is disposed between the left ventricle 12 and an aorta 20. A pulmonary or semi-lunar valve 26 is disposed between the right ventricle 14 and a pulmonary artery 24. A superior vena cava 28 and an inferior vena cava 30 return blood from the body to the right atrium 18. A mitral valve 32 is disposed between the left atrium 16 and the left ventricle 12. A tricuspid valve 34 is disposed between the right atrium 18 and the right ventricle 14. Pulmonary veins 36 return blood from the lungs to the left atrium 16. A left atrial appendage (LAA) 50 is attached to and in fluid communication with the left atrium 16.

Figure 2:
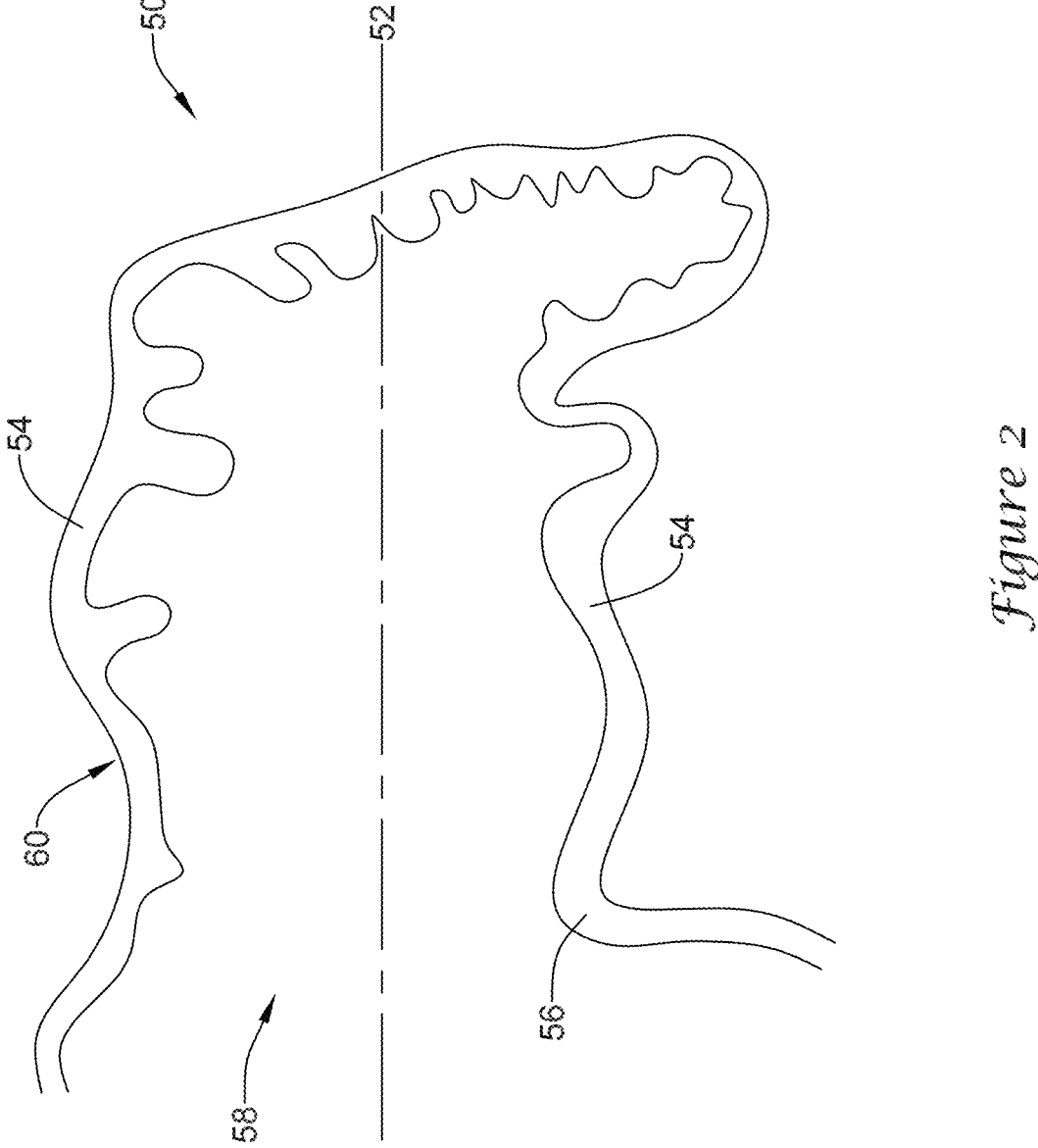
FIG. 2 is a schematic partial cross-sectional view of an example left atrial appendage.

FIG. 2 is a partial cross-sectional view of an example left atrial appendage 50. As discussed above, the left atrial appendage 50 may have a complex geometry and/or irregular surface area. Those skilled in the art will recognize that the illustrated LAA is merely one of many possible shapes and sizes for the LAA, which may vary from patient to patient. Those of skill in the art will also recognize that the medical devices and methods disclosed herein may be adapted for various sizes and shapes of the LAA, as necessary. A left atrial appendage 50 may include a generally longitudinal axis 52 arranged along a depth of a main body 60 of the left atrial appendage 50. The main body 60 may include a lateral wall 54 and an ostium 56 forming a proximal mouth 58. In some embodiments, a lateral extent of the ostium 56 and/or the lateral wall 54 may be smaller or less than a depth of the main body 60 along the longitudinal axis 52, or a depth of the main body 60 may be greater than a lateral extent of the ostium 56 and/or the lateral wall 54. In some embodiments, the left atrial appendage 50 may narrow quickly along the depth of the main body 60 or the left atrial appendage may maintain a generally constant lateral extent along a majority of depth of the main body 60. In some embodiments, the left atrial appendage 50 may include a distalmost region formed or arranged as a tail-like element associated with a distal portion of the main body 60. In some embodiments, the distalmost region may protrude radially or laterally away from the longitudinal axis 52.

Figure 3:
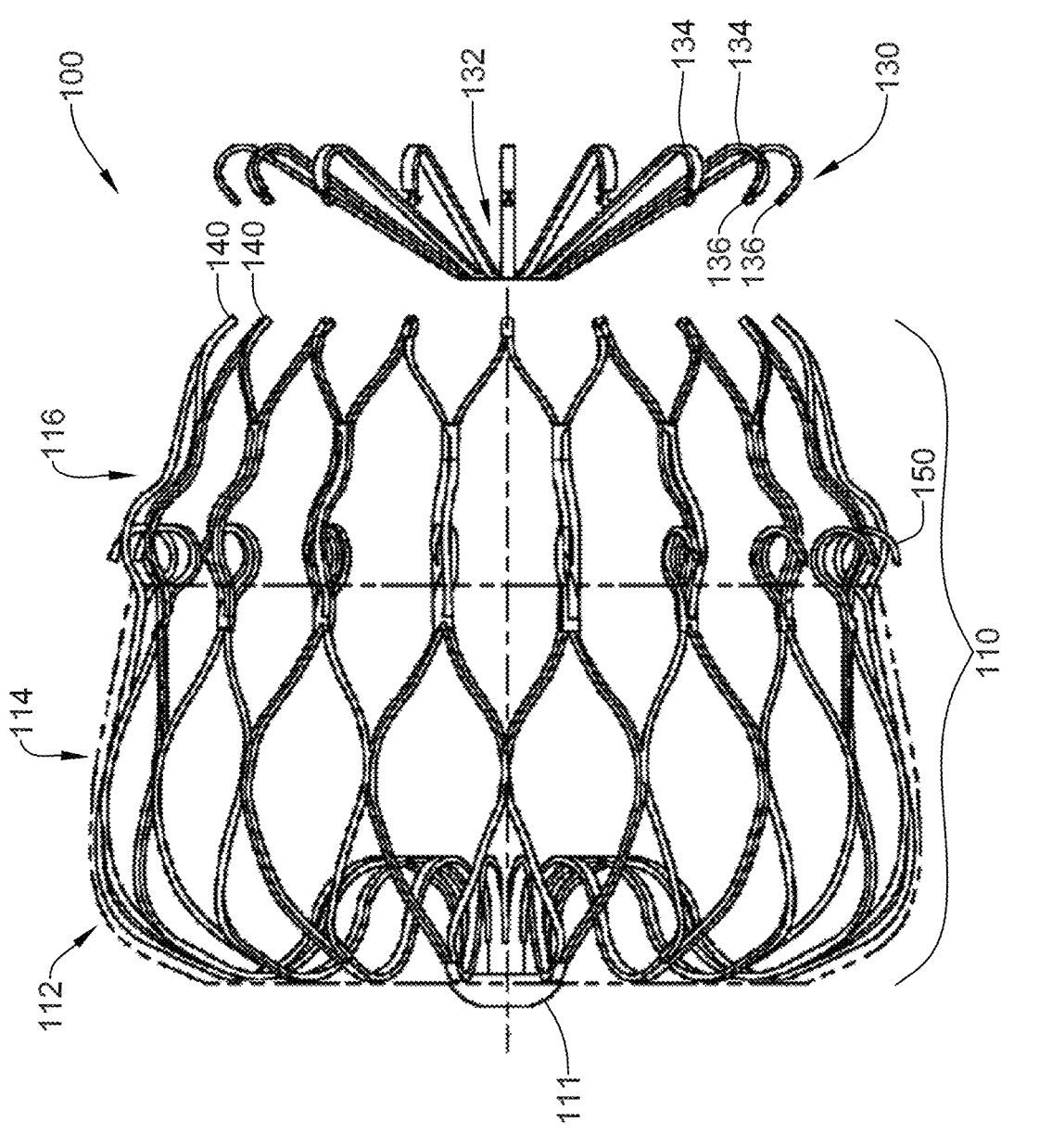
FIGS. 3-3A illustrate an example prior art implant.
Figure 3A:
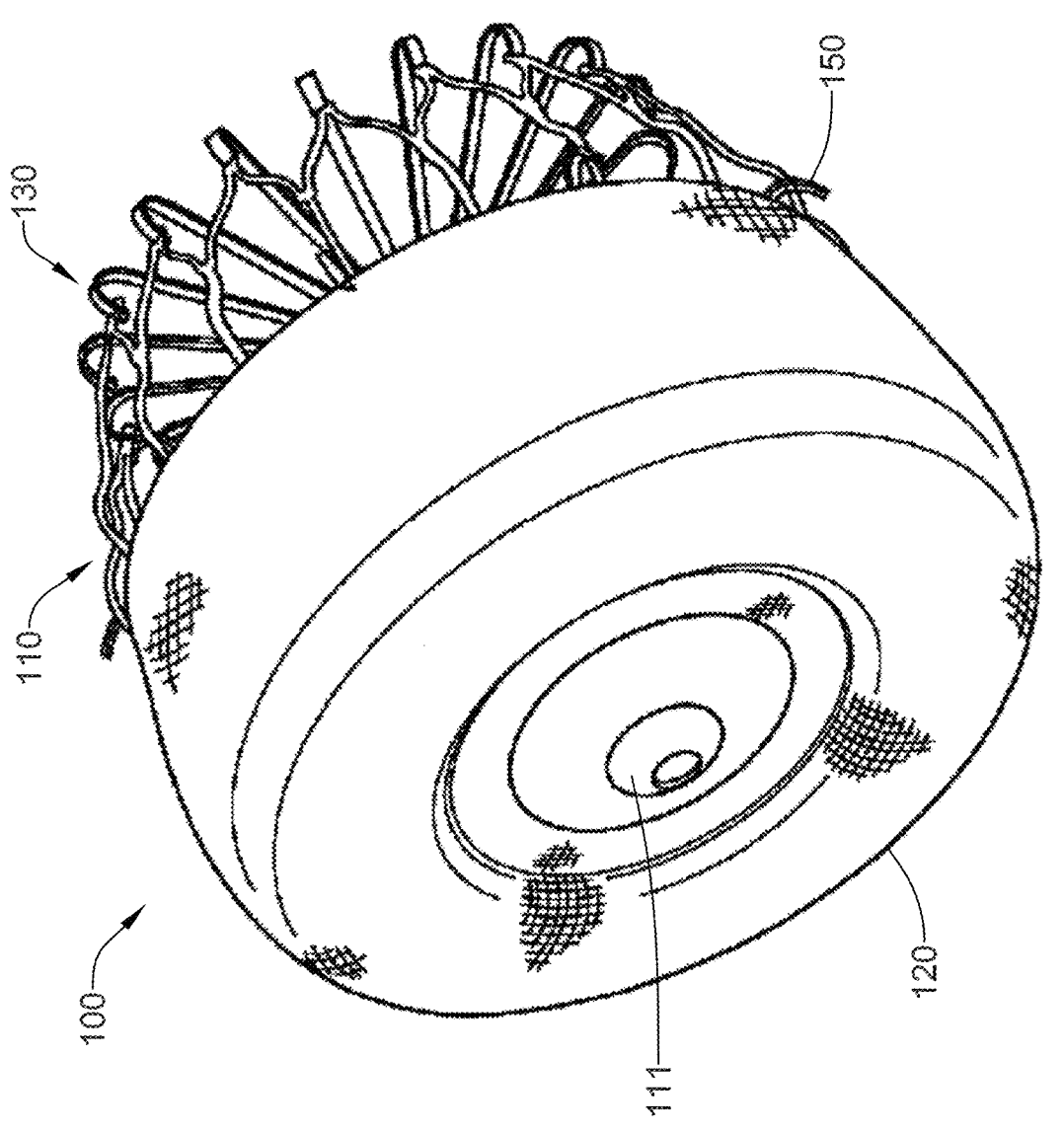

FIGS. 3 and 3A generally illustrate an example prior art implant 100, such as that disclosed in U.S. application Ser. No. 12/583,744, which is herein incorporated by reference. The implant 100 may generally comprise a support frame 110 partially covered by a membrane 120, and a distal cap 130. The support frame 110 may include proximal collar 111 and a plurality of struts forming a lattice of generally diamond-shaped wire portions extending therefrom. The support frame 110 may include a first row 112 of generally diamond-shaped wire portions, a second row 114 of generally diamond-shaped wire portions, and a third row 116 of elongated generally diamond-shaped wire portions. The support frame 110 may terminate at its distal end in a plurality of limbs 140. The distal cap 130 may attach to the terminating distal ends of the limbs 140. The support frame 110 may include a plurality of barbs 150 extending radially outward from the support frame 110 to penetrate tissue and inhibit longitudinal movement of the deployed implant 100 in a proximal direction. The barbs 150 may be generally arranged in a single row about the circumference of the support frame 110 and extending distally from a distal end of the second row 114 of diamond-shaped wire portions. The barbs 150 may each be disposed immediately alongside one strut forming one side portion of one elongated generally diamond-shaped wire portion of the third row 116.

The distal cap 130 includes a central hub 132 and a plurality of spokes 134 extending radially outward therefrom. The spokes 134 each have a first end 136 that attaches to a corresponding terminating distal end of one of the limbs 140. The central hub 132 remains positioned proximal of the terminating distal ends of the limbs 140 at all operational positions of the implant 100. Additionally, at no point during the operation of the implant 100 does any portion of the plurality of struts extend distally of the terminating distal ends of the limbs 140. That is, the terminating distal ends of the limbs 140 are the distalmost element of the plurality of struts and/or the support frame 110.

Figure 4A:
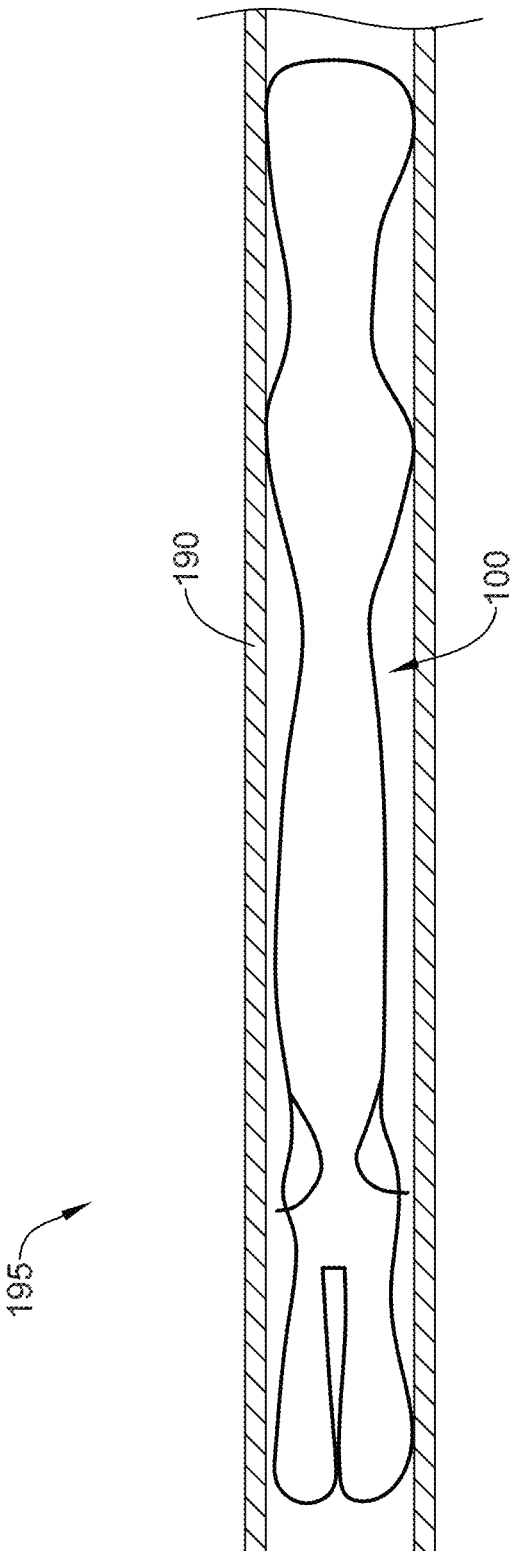
FIG. 4A is a partial cross-sectional view of the example prior art implant of FIGS. 3-3A in a first, constrained position.
Figure 4B:
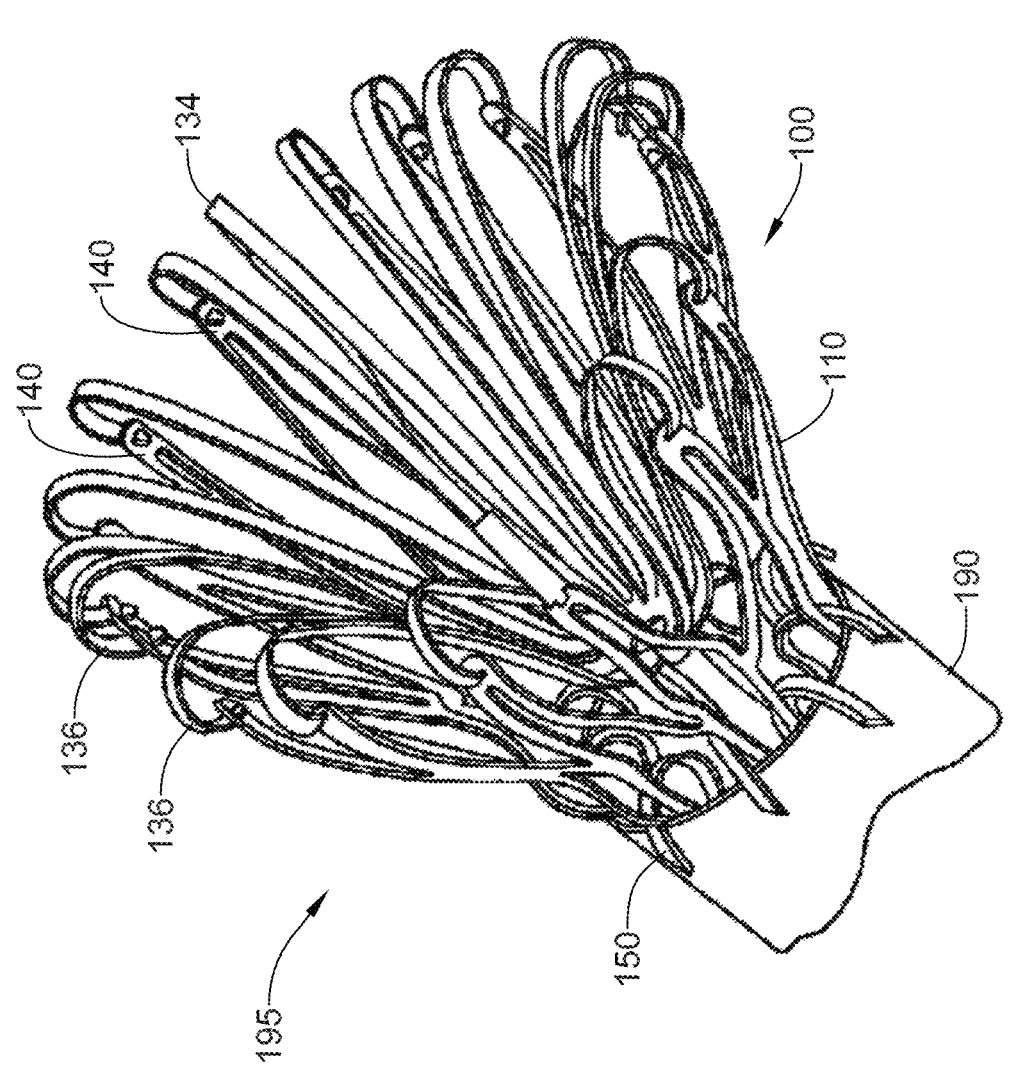
FIGS. 4B-4D illustrate perspective views of the example prior art implant of FIGS. 3-3A in various stages of deployment.
Figure 4C:
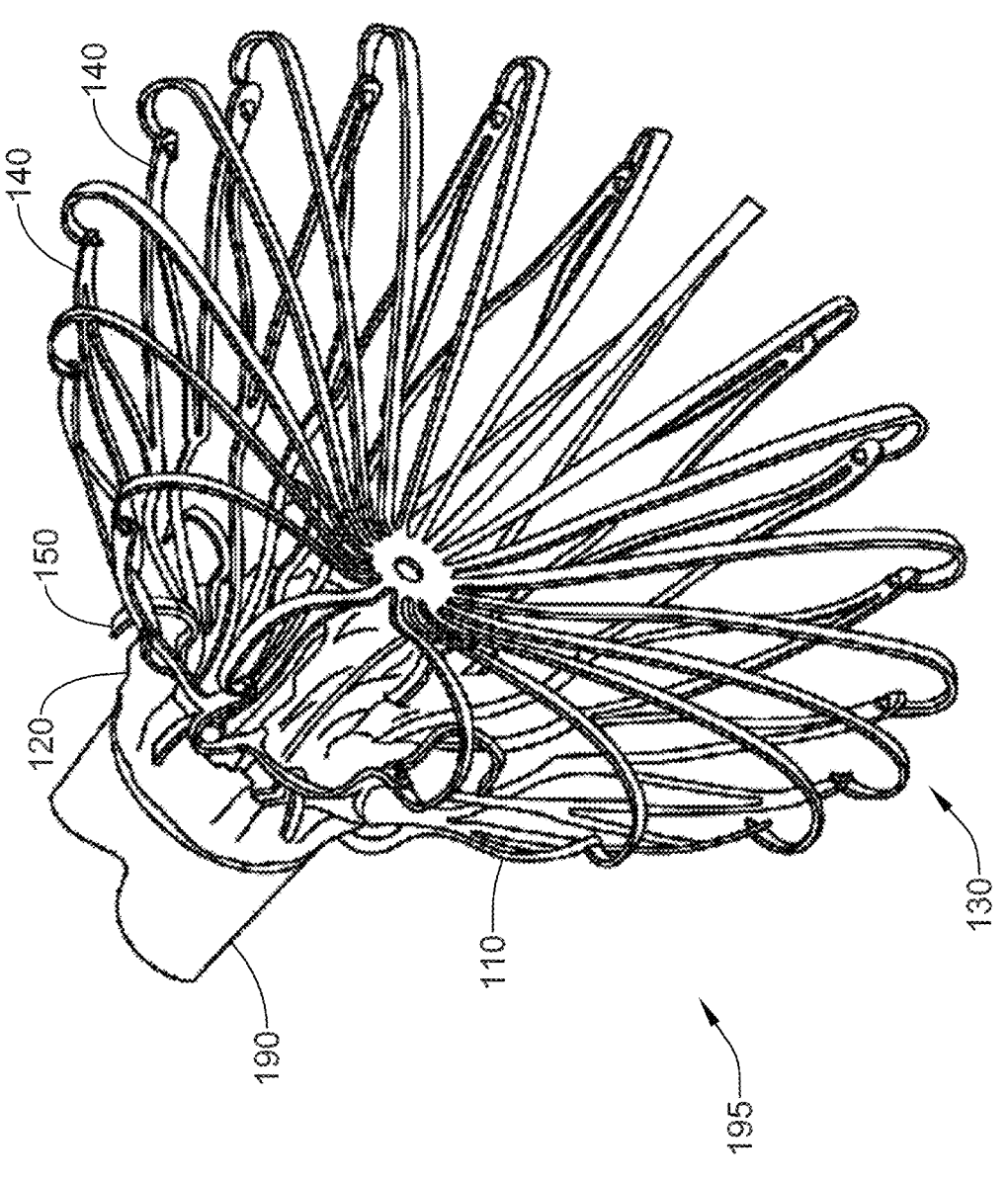
Figure 4D:
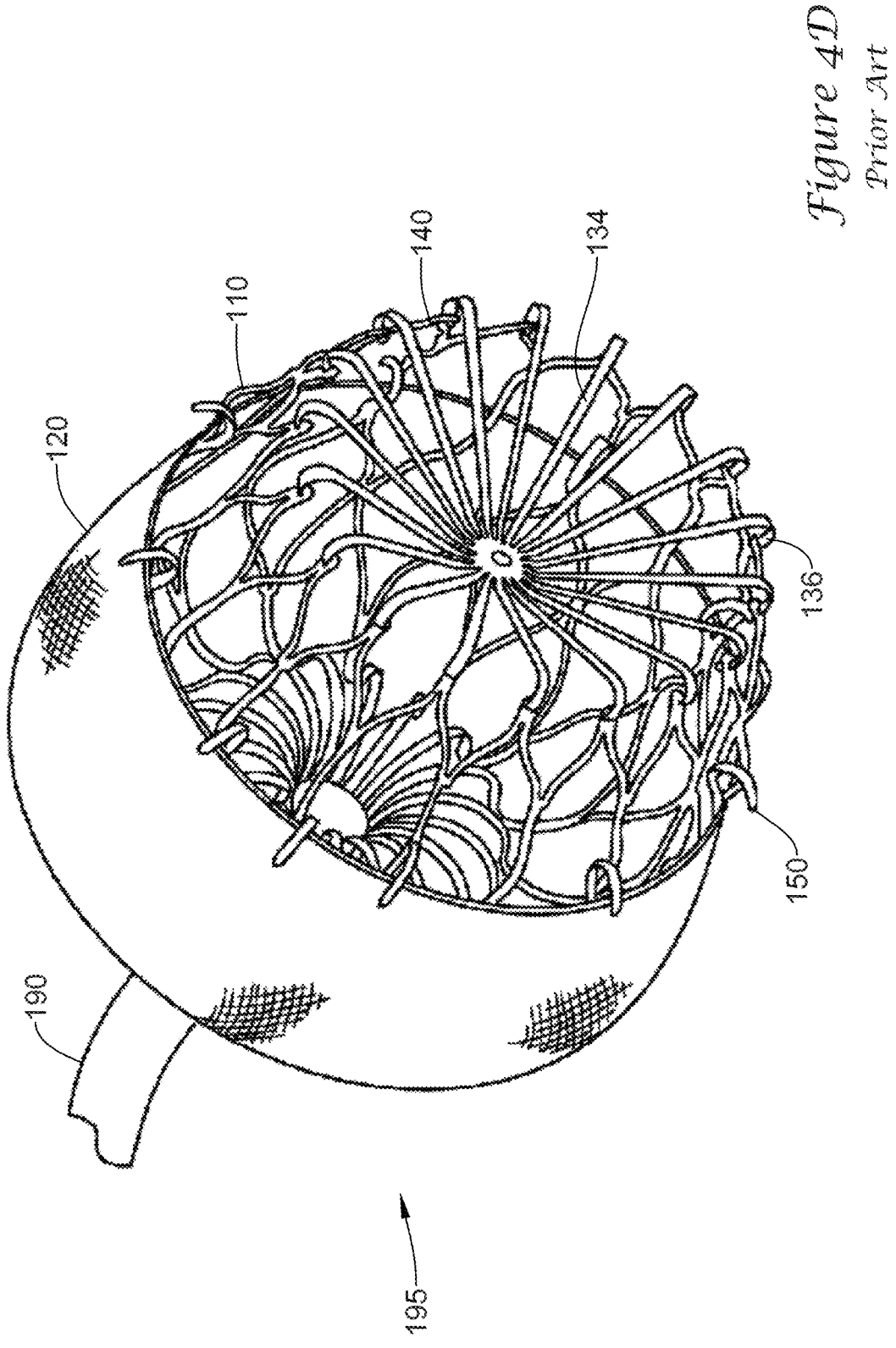

Turning to FIGS. 4A-4D, during delivery of the example prior art implant 100 into a left atrial appendage, the implant 100 may be disposed within a delivery catheter 190 to collectively form a medical device 195. The medical device 195 may be percutaneously inserted into a patient to deliver the implant 100 to the left atrial appendage. Initially, the implant 100 may be disposed in a first, constrained position, such that the support frame 110 fits within the lumen of the delivery catheter 190, as seen in FIG. 4A. Upon reaching the left atrial appendage, the delivery catheter 190 may be withdrawn proximally to expose the implant 100. As the delivery catheter 190 is withdrawn, the terminating distal ends of the limbs 140 and the first ends 136 of the spokes 134 are exposed and expand radially outward. As seen in FIG. 4B, when the barbs 150 reach the distal end of the delivery catheter 190, the terminating distal ends of the limbs 140 and the first ends 136 have extended radially outward to a second, flowering position. Continuing to withdrawn the delivery catheter 190, the distal cap 130 fully deploys radially outward, pulling the terminating distal ends of the limbs 140 radially outward to a third, mid-deployment position, as seen in FIG. 4C. Next, the delivery catheter 190 is completely withdrawn from the implant 100 so that the implant 100 may assume a fourth, expanded position where the support frame 110 may extend radially outward from a central longitudinal axis farther than the terminating distal ends of the limbs 140 and/or the first ends 136 of the spokes 134, as seen in FIG. 4D. The implant 100, in the fourth expanded position, pushes outward to "drive" into the tissue such that the tissue conforms to the shape of the outer surface of the implant 100. Lastly, the delivery catheter 190 and/or a delivery shaft (not shown) disposed therein may be disconnected from the proximal collar 111 and removed from the patient.

Applicants have found that recapture of the implant may be made easier by staggering the barbs into multiple rows such that less distally-directed force is required for the delivery catheter to remove any given row from the tissue of the left atrial appendage. Additionally, changes in geometry to certain aspects of the implant may permit the use of more-compliant struts that also facilitate easier recapture and repositioning of the implant while maintaining at least the same amount of radially outward force at each of the barbs/anchors, and providing improved conformability to and sealing with the geometry of the left atrial appendage. Further still, changes in geometry at the distal end of the implant may facilitate use in shorter left atrial appendages, as well as easier and cheaper manufacturing of the implant, for example, avoiding manual assembly of the spokes to the limbs and/or individual laser welds to each of these joints. Accordingly, an example implant is disclosed herein, which may incorporate some or all of these changes.

Figure 5:
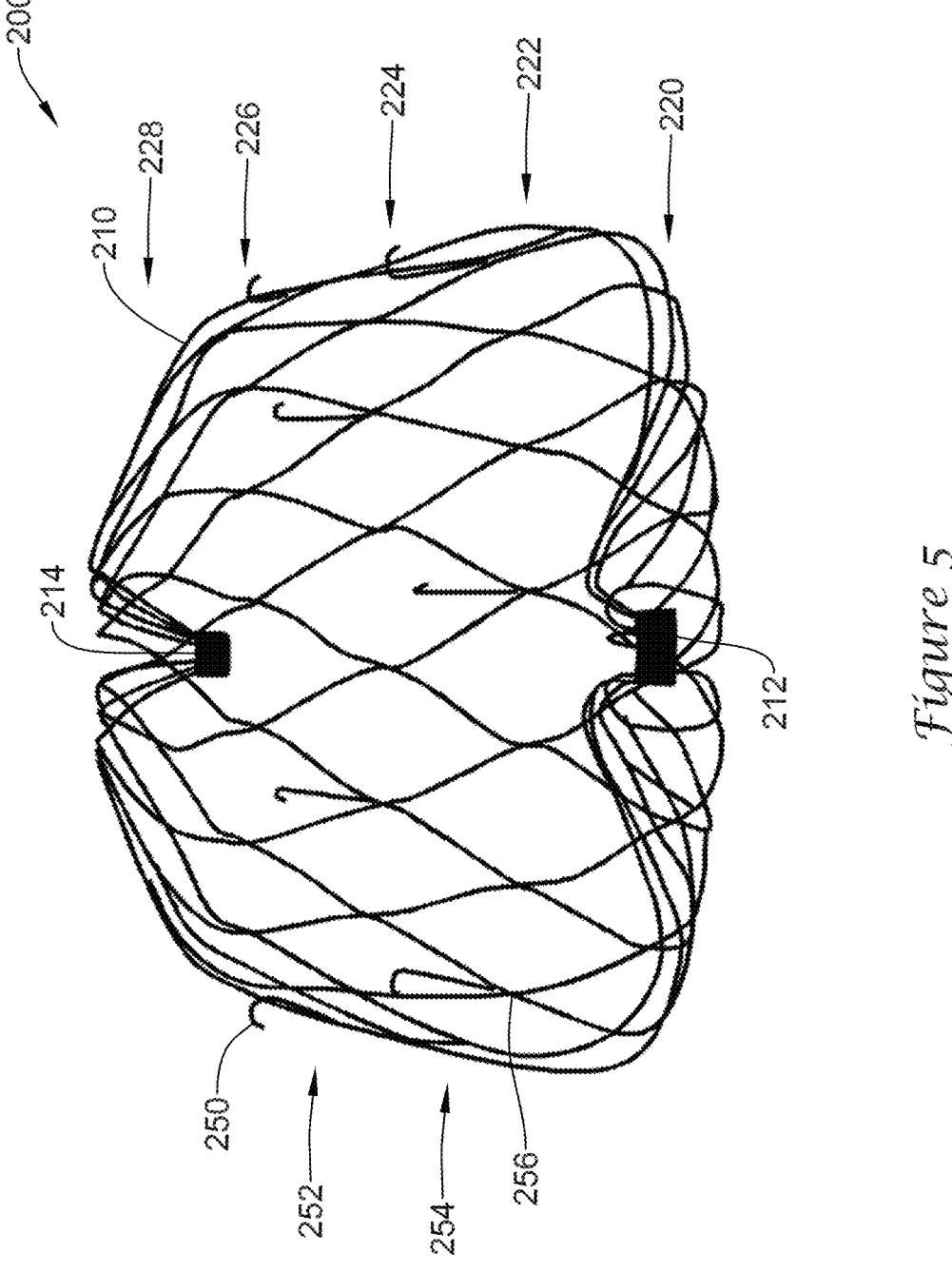
FIG. 5 illustrates a portion of an example medical device according to the present disclosure.

FIG. 5 illustrates a perspective view of a portion of an example implant 200. The implant 200 may include a self-expanding monolithic support frame 210 extending from a proximal collar 212 to a distal collar 214. In some embodiments, the support frame 210 may include a plurality of struts forming a lattice of generally diamond-shaped wire portions. In some embodiments, the support frame 210 may include, generally extending from proximally to distally, a first row 220 of generally diamond-shaped wire portions, a second row 222 of generally diamond-shaped wire portions adjacent the first row 220, a third row 224 of generally diamond-shaped wire portions adjacent the second row 222, a fourth row 226 of generally diamond-shaped wire portions adjacent the third row 224, and a fifth row 228 of generally diamond-shaped wire portions adjacent the fourth row 226. In some embodiments, a plurality of legs may extend from the proximalmost and/or distalmost row(s) of generally diamond-shaped wire portions to the proximal and/or distal collar(s), respectively. In some embodiments, the proximalmost and/or distalmost row(s) of generally diamond-shaped wire portions may be attached directly to the proximal and/or distal collar(s), respectively. As will be appreciated by the skilled artisan, additional or fewer rows of generally diamond-shaped wire portions may be included in the support frame 210. Increasing the number of rows of generally diamond-shaped wire portions may permit a thinner strut thickness to be used, which may result in greater flexibility, compliance, and conformability of the plurality of struts and/or the support frame 210. In other words, when deployed, the support frame 210 may substantially conform to an internal geometry and/or shape of the lateral wall of the left atrial appendage, rather than forcing the lateral wall to conform to the shape of the support frame.

In some embodiments, the support frame 210 may include a plurality of anchors 250 provided to secure the implant 200 to the lateral wall of the left atrial appendage after deployment and thereby inhibit proximal movement of the implant 200 relative to the left atrial appendage. In some embodiments, the plurality of anchors 250 may be arranged into a first row 252 of anchors and a second row 254 of anchors disposed proximally of the first row 252 of anchors, wherein the first row 252 of anchors and the second row 254 of anchors cooperate to form a staggered pattern about the circumference of the support frame 210. Each of the plurality of anchors 250 may extend distally from a strut node junction 256, such that a hook portion of each of the plurality of anchors 250 is positioned within an interior of one generally diamond-shaped wire portion, spaced apart from the adjacent struts. While not explicitly shown, additional rows or other alternate arrangements of the plurality of anchors 250 are also possible. In some embodiments, the plurality of anchors 250 may be equally spaced apart from each other. In some embodiments, the plurality of anchors 250 may be spaced an unequal intervals or distances from each other. In some embodiments, the staggered pattern may be uniform, such that angles and distances between adjacent anchors are the same. In some embodiments, the staggered pattern may be non-uniform, such that some or all angles and distances between adjacent anchors are different. The staggered pattern may provide improved fixation strength, improved apposition to adjacent tissue, a reduced profile in a first, constrained position, reduced force required to remove the plurality of anchors 250 from the tissue (compared to placing all of the anchors in a single row) since only a portion of the total anchors is removed at a time, and reduced force required to retrieve the implant 200 back into a delivery catheter for repositioning (compared to having all of the anchors in a single row). Transition of the implant 200 from the first, constrained position to a second, flowering position to a third, mid-deployment position to a fourth, unconstrained position will be described in more detail below.

Figure 6:
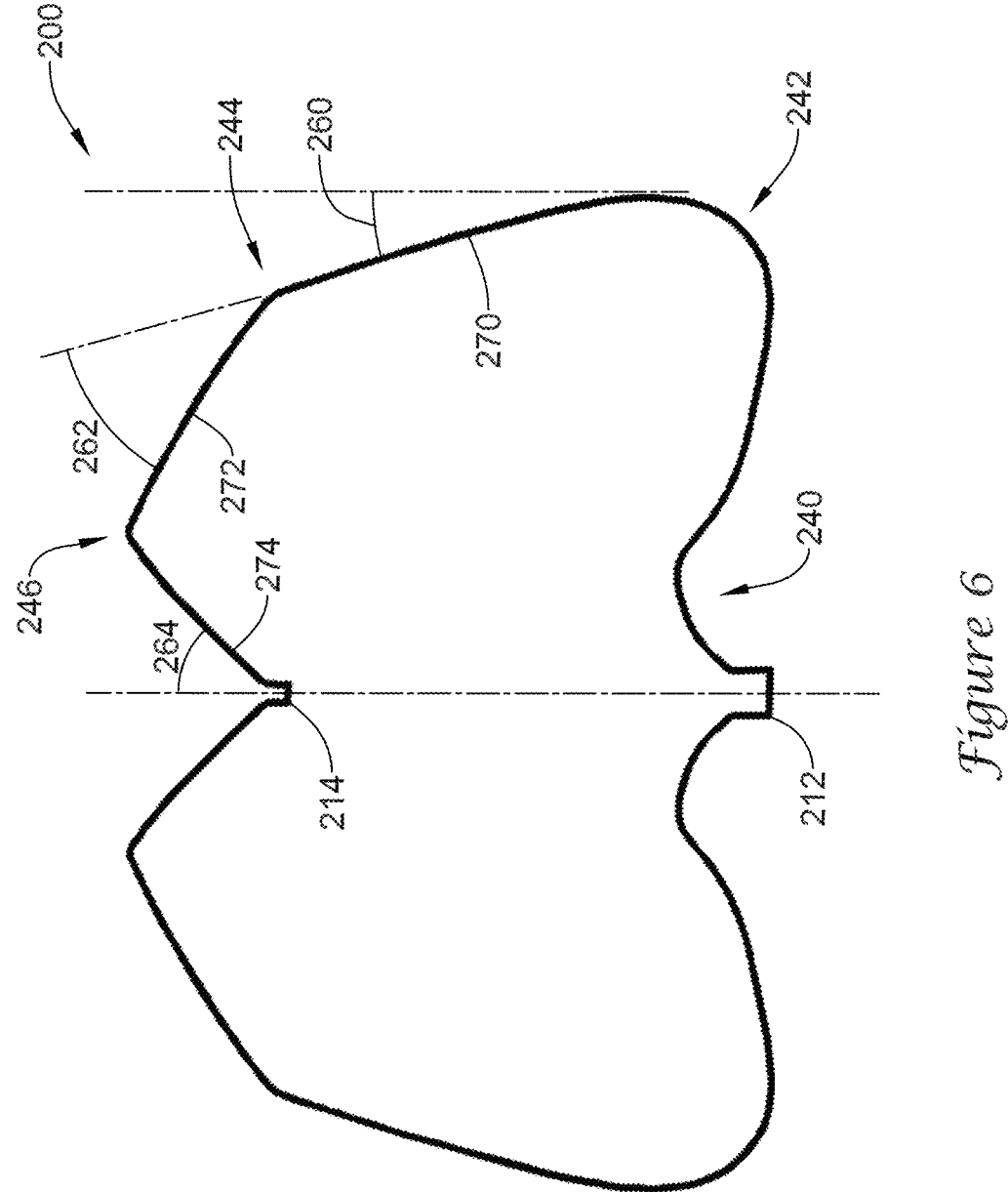
FIG. 6 is a partial cross-sectional view of the example medical device of FIG. 5.

FIG. 6 illustrates a cross-sectional view of a profile of the implant 200 and/or the support frame 210 in a fourth, unconstrained position. In the cross-sectional view, certain features of the profile can be described. In the fourth, unconstrained position, the profile extends distally from the proximal collar 212 and curves radially outward at a first bend 240 adjacent the proximal collar 212. The first bend 240 forms a serpentine-like S-shape as the profile extends radially outward to a second bend 242. At the second bend 242, the profile turns distally and radially inward, such that a first segment 270 of the profile forms a first angle 260 with a reference plane tangent to the second bend 242 and parallel to a central longitudinal axis of the implant 200. In some embodiments, the first angle 260 may be in a range from about 5 degrees to about 25 degrees, or about 10 degrees to about 20 degrees. In some embodiments, the second bend 242 may include a short generally straight segment (about 0.025 inches to about 0.150 inches long) extending distally along the reference plane and an intermediate bend turning radially inward, such that the first segment 270 extends distally and radially inward from the intermediate bend. The first segment 270 extends distally and radially inward from the second bend 242 (and/or the intermediate bend) to a third bend 244, where the profile turns radially inward at a sharper angle while still extending distally, such that a second segment 272 of the profile forms a second angle 262 with the first segment 270 of the profile (and/or a reference plane tangent thereto). In some embodiments, the second angle 262 may be in a range from about 20 degrees to about 65 degrees, about 30 degrees to about 60 degrees, or about 40 degrees to about 50 degrees. The second segment 272 extends distally and radially inward from the third bend 244 to a fourth bend 246 adjacent the distal collar 214. At the fourth bend 246, the profile turns proximally and continues radially inward to the distal collar 214, such that a third segment 274 of the profile (and/or a reference plane tangent thereto) forms a third angle 264 with the central longitudinal axis. In some embodiments, the third angle 264 may be in a range from about 35 degrees to about 75 degrees, about 40 degrees to about 65 degrees, or about 45 degrees to about 60 degrees. The third segment 274 extends proximally and radially inward from the fourth bend 246 to the distal collar 214. The first segment 270 may have a first length, the second segment 272 may have a second length, and the third segment 274 may have a third length. The length of the second segment 272 and the length of the third segment 274 may be compared as a ratio. In some embodiments, the ratio of the length of the second segment 272 to the length of the third segment 274 (i.e., second length divided by third length) may be about 0.850 to about 2.160, about 1.000 to about 1.600, or about 1.100 to about 1.300. As may be seen from the profile illustrated in FIG. 6, the distal ends of the plurality of struts of the support frame 210 (at the distal collar 214) may be disposed proximal of a distalmost portion of the plurality of struts of the support frame 210 and/or the implant 200. In some embodiments, an overall length of the implant 200 from a proximalmost portion to a distalmost portion, as measured along a line parallel to the central longitudinal axis, may be from about 0.800 inches to about 0.900 inches, or about 0.830 inches, in the fourth, unconstrained position. In some embodiments, a center of a radius forming the third bend 244 may be located, as measured along a line parallel to the central longitudinal axis, about 0.050 inches to about 0.360 inches, or about 0.130 inches to about 0.240 inches, or about 0.160 to about 0.180 inches proximal of the distalmost portion, in the fourth, unconstrained position. Additional constructional details may be found with the discussion directed to FIGS. 10 and 10A below.

Figure 7:
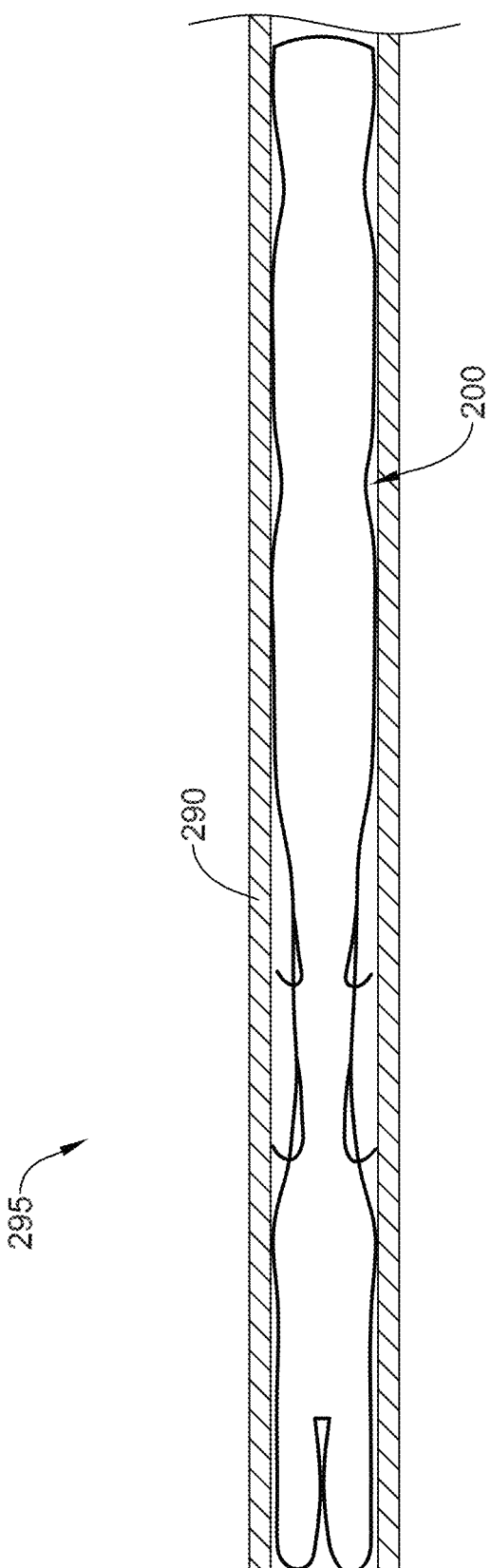
FIG. 7 is a partial cross-sectional view of the example medical device of FIG. 5 in a first, constrained position.
Figure 8:
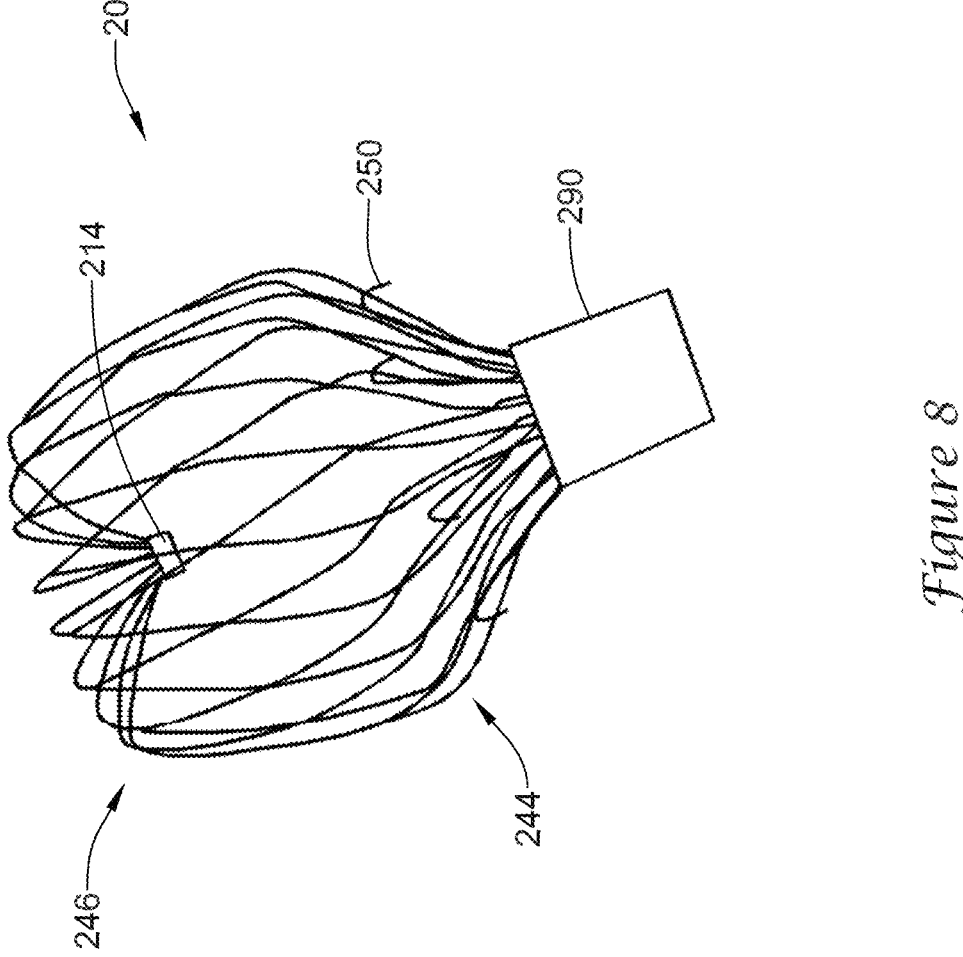
FIG. 8 illustrates the example medical device of FIG. 5 partially deployed.
Figure 9:
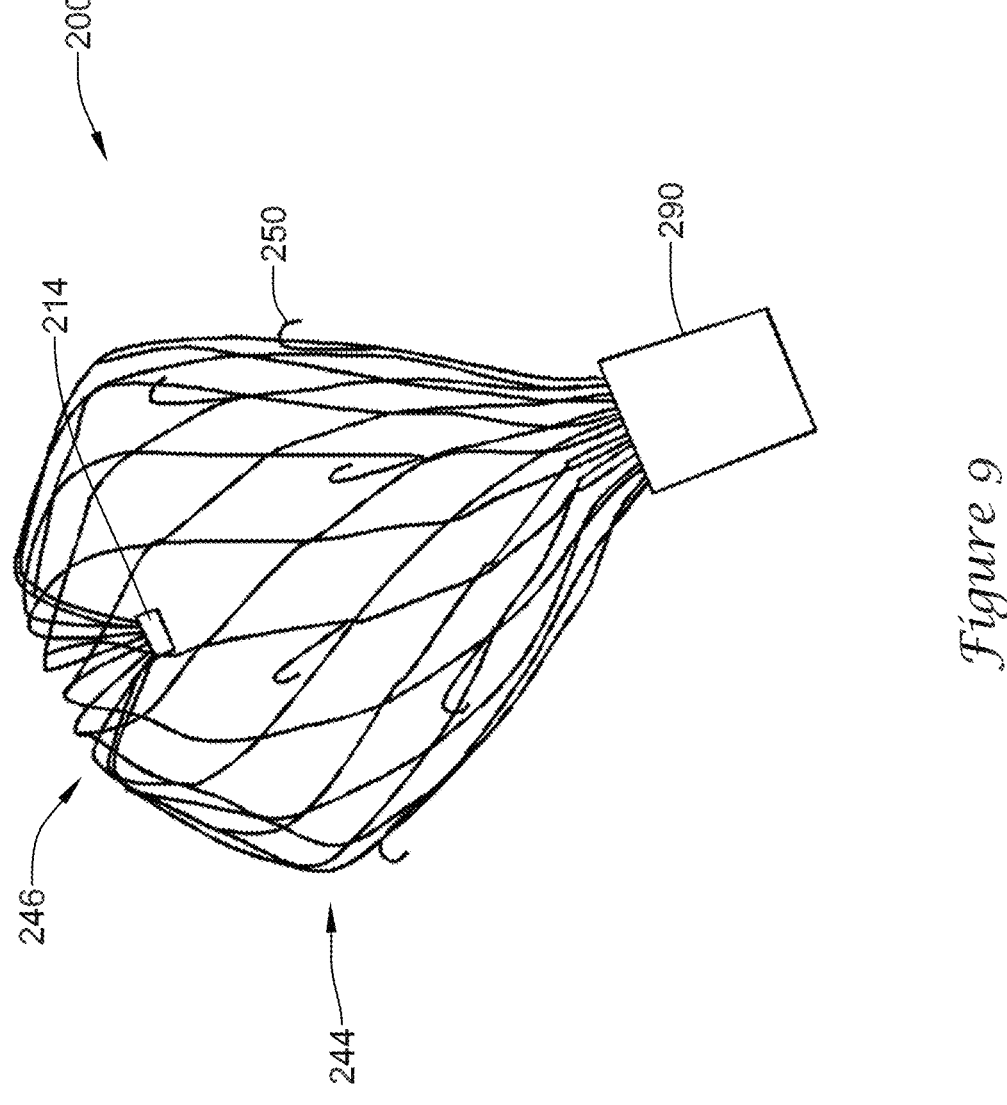
FIG. 9 illustrates the example medical device of FIG. 5 partially deployed.

Turning to FIGS. 7-9, the implant 200 is illustrated in different stages of deployment. During delivery of the implant 200 to a left atrial appendage, the implant 200 may be disposed within a lumen of a delivery catheter 290 to collectively form a medical device 295. The medical device 295 may be percutaneously inserted into a patient to deliver the implant 200 to the left atrial appendage. Initially, the implant 200 may be disposed in a first, constrained position, with the first bend 240, the second bend 242, and the third bend 244 substantially straightened into an elongated shape such that the support frame 210 fits within the lumen of the delivery catheter 290 with the second segment 272 and the third segment 274 generally parallel to each other, as seen in FIG. 7. A delivery shaft (not shown) disposed within the lumen of the delivery catheter 290 may be removably connected to the implant 200 at the proximal collar 212. Upon reaching the left atrial appendage, the delivery catheter 290 may be withdrawn proximally while the delivery shaft is held stationary, or the delivery shaft may be advanced distally while the delivery catheter 290 is held stationary (i.e., relative movement between the delivery catheter and the delivery shaft may be used), to expose the implant 200 within the left atrial appendage. As the delivery catheter 290 is withdrawn, the fourth bend 246 extends from a distal end of the delivery catheter 290 first with the distal collar 214 disposed proximal of the fourth bend 246.

As the delivery catheter 290 is withdrawn, the support frame 210 is exposed and expands radially outward slightly at the fourth bend 246. Next, as seen in FIG. 8, as the third bend 244 exits the delivery catheter 290, or about when the plurality of anchors 250 initially begins to exit the distal end of the delivery catheter 290, the fourth bend 246 is opened compared to the first, constrained position, and the second segment 272 and the third bend 244 are translated radially outward compared to the first, constrained position, such that the second segment 272 angles distally and radially inward from the third bend 244 toward the fourth bend 246 to define a second, flowering position, wherein the exposed support frame 210 generally resembles a tulip. In the second, flowering position, the implant 200 is partially disposed within the lumen of the delivery catheter 290, with a portion of the first segment 270 and the second bend 242 remaining positioned within the lumen of the delivery catheter 290. In the second, flowering position, the first row 252 of anchors 250 may be disposed outside of the lumen of the delivery catheter 290 and the second row 254 of anchors 250 may be disposed inside of the lumen of the delivery catheter 290. In the second, flowering position, the plurality of anchors 250 may be prevented from engaging surrounding tissue (i.e., the lateral wall) of the left atrial appendage. At this stage of deployment, positioning of the implant 200 within the left atrial appendage may be adjusted without having to remove anchors from tissue.

Continuing to withdraw the delivery catheter 290, a proximal end of the second segment 272 and the third bend 244 is translated radially outward and distally relative to the fourth bend 246 (and/or compared to the second, flowering position) to a third, mid-deployment position. In the third, mid-deployment position, the third bend 244 constitutes a portion of the support frame 210 that defines a lateralmost extent from the central longitudinal axis, as seen in FIG. 9. Similarly, the fourth bend 246 widens or opens laterally as the third bend 244 translates distally. In the third, mid-deployment position, the first segment 270 extends distally and radially outward from the second bend 242 toward the third bend 244. In the third, mid-deployment position, the second segment 272 extends less distally (i.e. extends a shorter longitudinal distance) and more radially inward (i.e., extends along a greater lateral or radial distance from the central longitudinal axis) from the second bend 242 toward the third bend 244 than in the second, flowering position. In the third, mid-deployment position, the first row 252 of anchors 250 may be disposed outside of the lumen of the delivery catheter 290 and the second row 254 of anchors 250 may be disposed outside of the lumen of the delivery catheter 290. In the third, mid-deployment position, the first row 252 of anchors 250 may engage tissue (i.e., the lateral wall) of the left atrial appendage sufficiently to be effective, and the second row 254 of anchors 250 may or may not engage tissue of the left atrial appendage. At this stage of deployment, positioning of the implant 200 within the left atrial appendage may be adjusted by removing the first row 252 of anchors 250 from tissue prior to adjustment. For a given quantity of anchors, having more than one row of anchors requires less axially-directed force to remove each individual row of anchors from the tissue than having all of the anchors in a single row.

Figure 12:
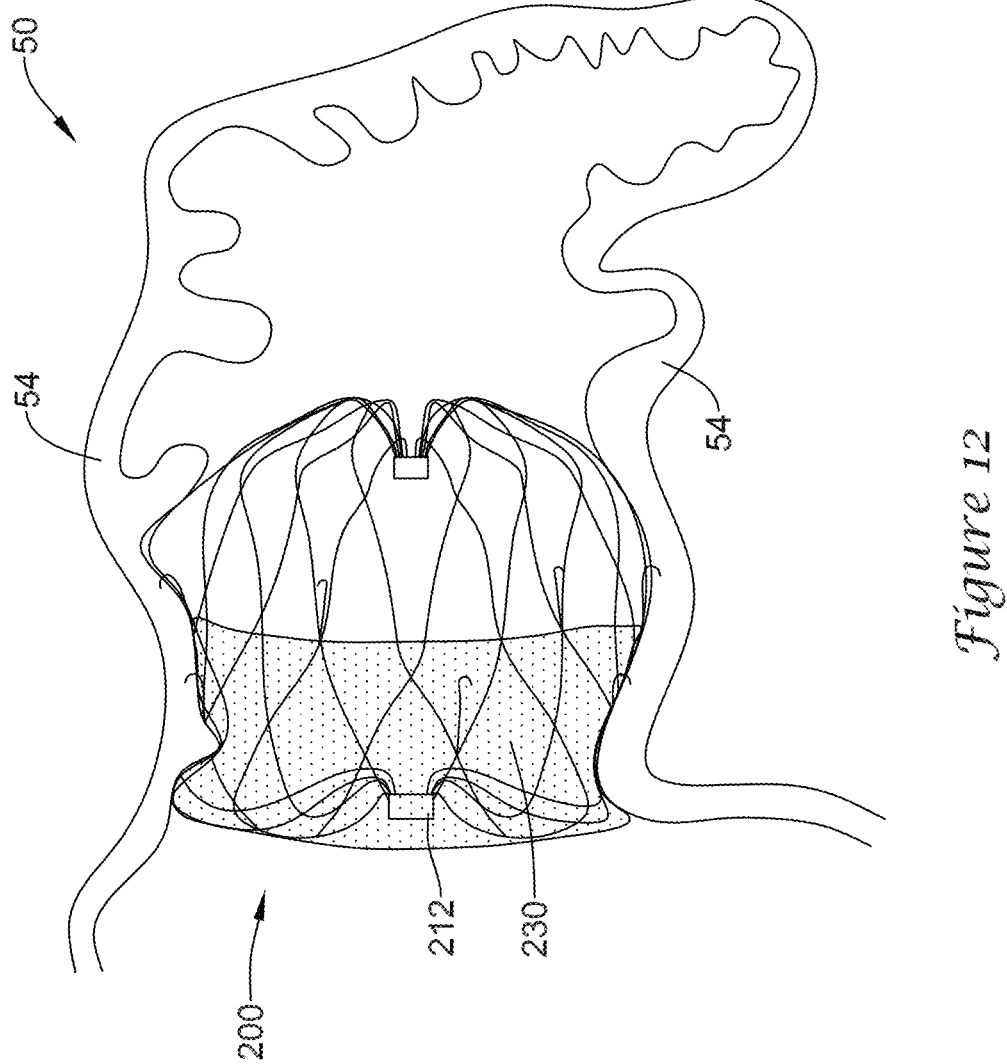
FIG. 12 is a partial cross-sectional view of the example medical device of FIGS. 5 and 11 deployed within the example left atrial appendage of FIG. 2.

Next, the delivery catheter 290 is completely withdrawn from the implant 200 so that the implant 200 is disposed outside of the delivery catheter 290 and may assume a fourth, unconstrained position where the support frame 210 at the second bend 242 may extend laterally or radially outward from the central longitudinal axis farther than at the third bend 244, as seen in FIGS. 5 and 6, to define a widest lateral extent of the implant 200. In the fourth, unconstrained position, the implant 200 may assume the profile discussed above with respect to FIGS. 5 and 6. During use and implantation, the implant 200, in some embodiments, may assume a deployed position wherein the implant 200 substantially conforms to the geometry of the left atrial appendage, as illustrated in FIG. 12. Lastly, the delivery catheter 190 and/or a delivery shaft (not shown) slidably disposed therein may be disconnected from the proximal collar 111 and removed from the patient.

Figure 10:
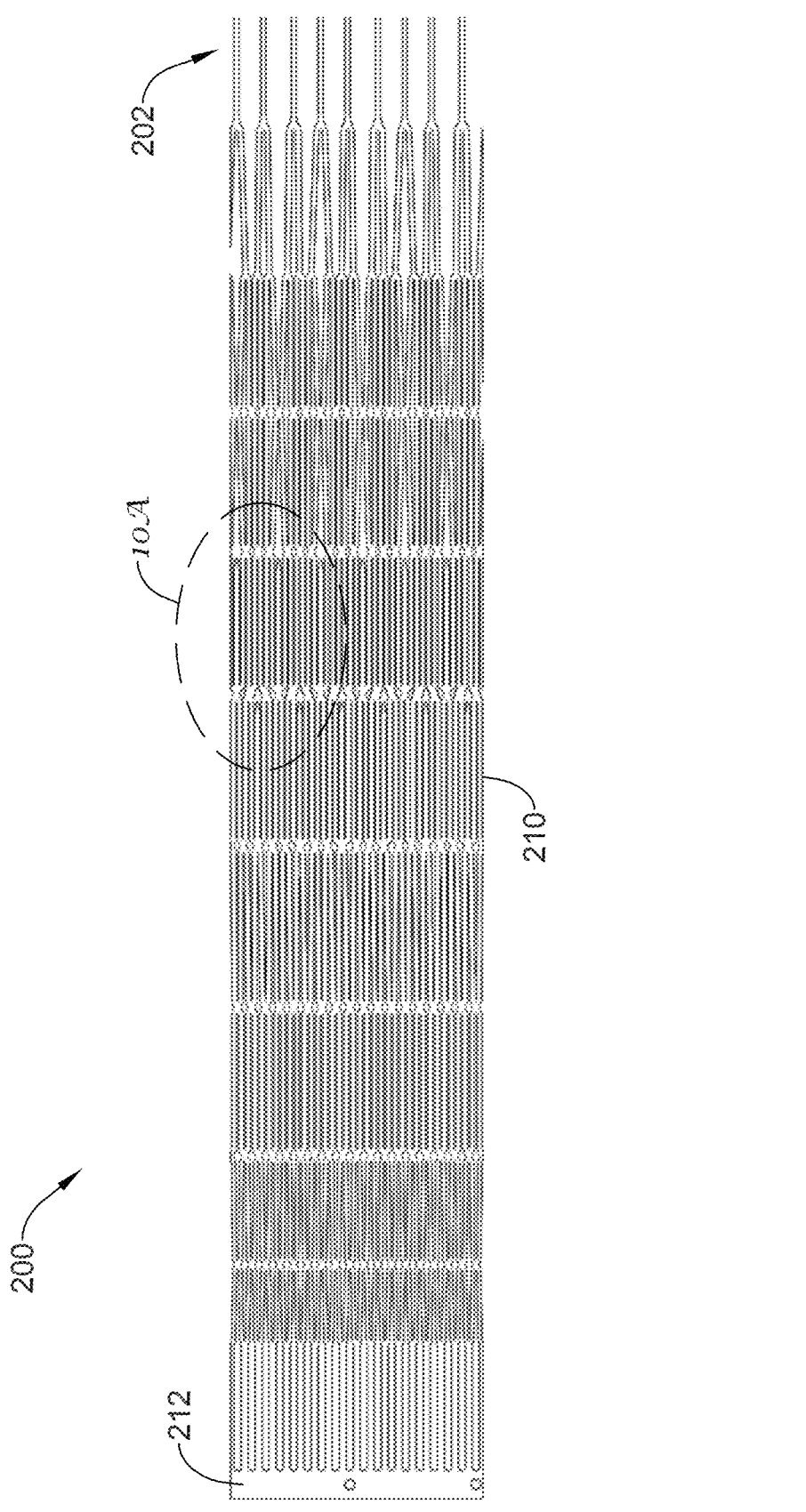
FIG. 10 illustrates the example medical device of FIG. 5 during manufacture in a flat-pattern view.

FIG. 10 illustrates the support frame 210 in an unrolled 2-D flat-pattern view, as cut from a tubular member, such as a metallic hypotube, or other suitable starting substrate. In some embodiments, the monolithic support frame 210 may be laser cut from a single tubular member. The skilled artisan will recognize that other manufacturing methods known in the art may be used including, but not limited to, machining, chemical etching, water cutting, EDM, etc. In some embodiments, the proximal collar 212 may be integrally formed with the support frame 210 and/or the plurality of struts. In some embodiments, after cutting the support frame 210, a plurality of free distal ends 202 may be fixedly attached to the distal collar 214. In some embodiments, the distal collar 214 may be formed as an annular ring member having an outer diameter smaller than an outer diameter of the tubular member and/or the proximal collar 212, for example, as seen in FIG. 7. The plurality of free distal ends 202 may be inserted into an interior of the distal collar 214 and fixedly attached thereto, for example, by adhesive(s), welding or soldering, friction fit, or other mechanical means. In some embodiments, the plurality of free distal ends 202 may be formed and inserted into a distal end of the distal collar 214, such that the plurality of struts extends distally from the distal collar 214. In some embodiments, a portion of the plurality of free distal ends 202 may extend through and/or proximally of the distal collar 214. In other words, the distal collar 214 may be disposed within an interior of the implant 200. The smaller outer diameter of the distal collar 214 facilitates a reduced profile in the first, constrained position.

Figure 10A:
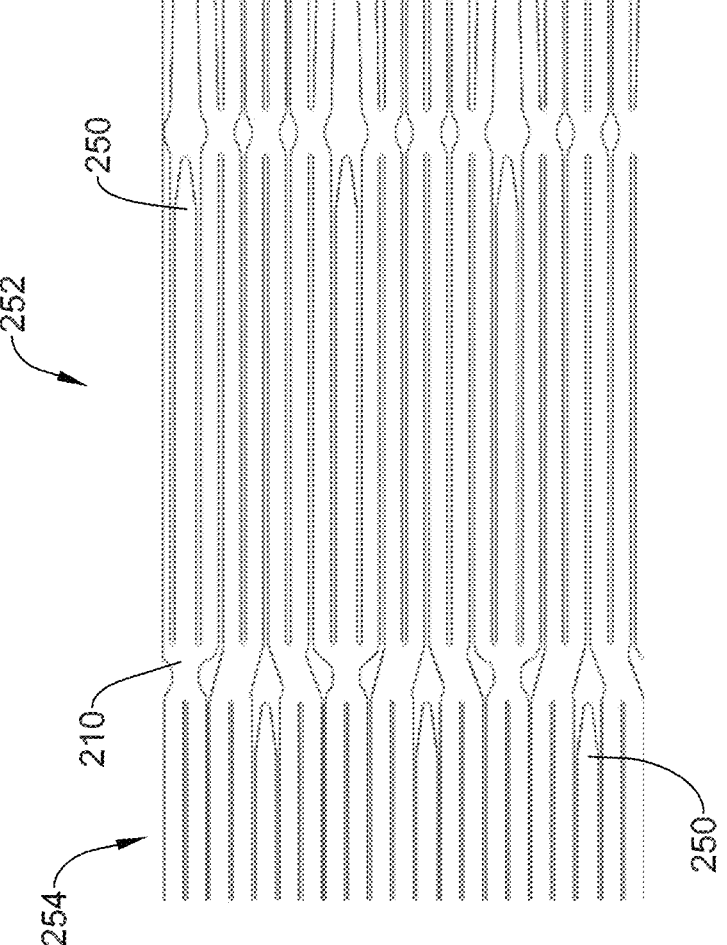
FIG. 10A is a detailed view of a portion of the example medical device shown in FIG. 10.

FIG. 10A shows a detailed view of a portion of the support frame 210 illustrated in FIG. 10. In the portion shown, one can see how the first row 252 and the second row 254 of anchors 250 may be formed. In some embodiments, such as shown in FIG. 10A, the plurality of anchors 250 may be integrally formed with the plurality of struts of the support frame 210 from a single tubular member, such that the plurality of anchors 250 is unitary with the support frame 210. In some embodiments, the plurality of anchors 250 may be manufactured separately and added at a later time, such as by adhesive(s), welding or soldering, or other known attachment means. Subsequent forming, bending, heat-treating, and/or other procedures may be performed on the support frame 210 in order to achieve a desired profile or shape, such as that shown in FIG. 6.

In some embodiments, a method of manufacturing the implant 200 may include the steps of:

obtaining an elongate tubular member having a lumen extending therethrough and an annular ring member;

laser cutting the tubular member to form a proximal collar, a plurality of struts, a plurality of anchors interspersed among the plurality of struts, and a plurality of free distal ends, as a single monolithic structure;

forming the plurality of struts into a lattice of generally diamond-shaped wire portions;

fixedly attaching the plurality of free distal ends to the annular ring member;

positioning the plurality of struts such that a cross-sectional profile of the left atrial appendage closure implant in an unconstrained position includes a first bend extending radially outward from the proximal collar to a second bend, a first segment extending distally and radially inward from the second bend to a third bend, a second segment extending distally and radially inward from the third bend to a fourth bend, and a third segment extending proximally and radially inward from the fourth bend to the annular ring member; and attaching a membrane over at least a portion of the plurality of struts such that the plurality of anchors extends through the membrane.

Figure 11:
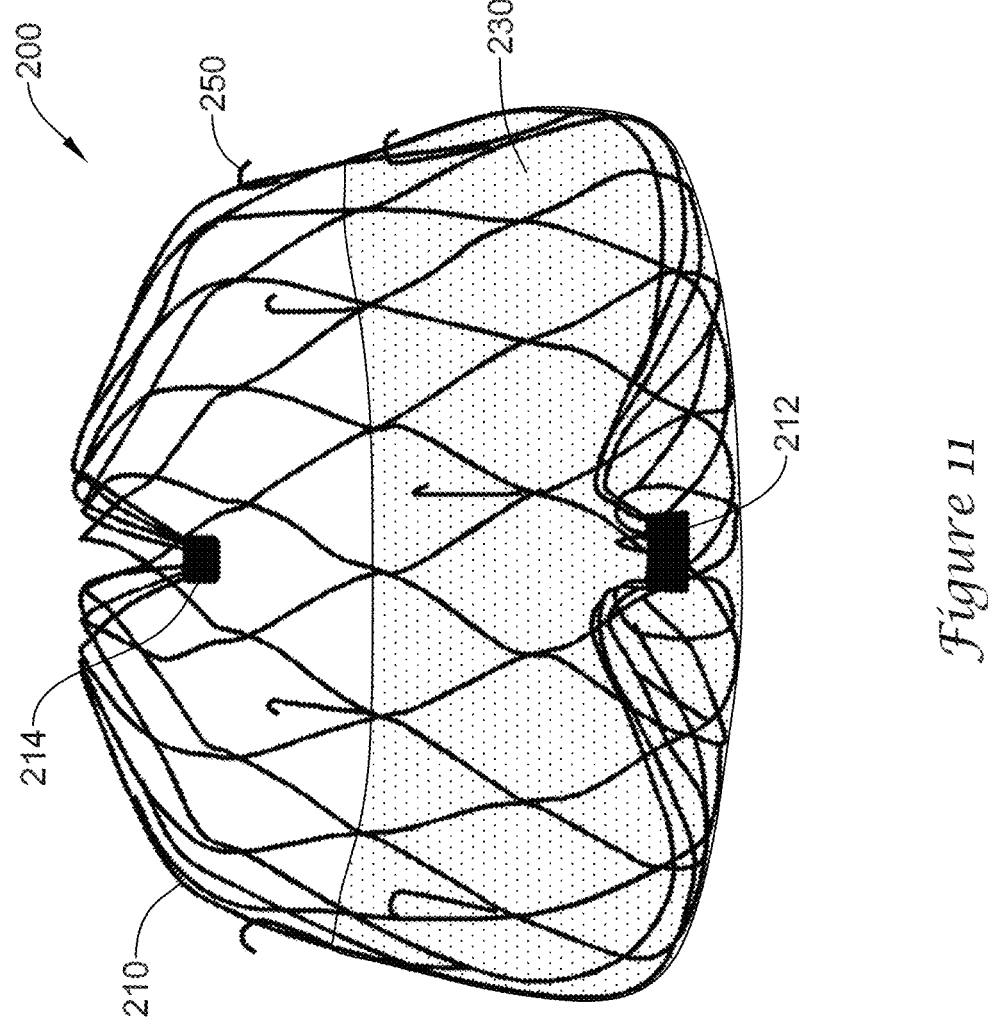
FIG. 11 illustrates a portion of the example medical device of FIG. 5.

FIG. 11 illustrates the example implant 200 having a membrane 230 disposed over at least a portion of the support frame 210. While not explicitly illustrated, the implant 200 shown in FIGS. 5-9 may include the membrane 230. In the interest of clarity, the membrane 230 was not shown in FIGS. 5-9. In some embodiments, at least some of the plurality of anchors 250 project through the membrane 230. In some embodiments, the membrane 230 may be attached to the support frame 210 at each anchor 250, for example, by passing each anchor 250 through the membrane 230, such as through a pore or aperture. In some embodiments, the membrane 230 may be attached to the support frame 210 by other suitable attachment means, such as but not limited to, adhesive(s), sutures or thread(s), welding or soldering, or combinations thereof. In some embodiments, the membrane 230 may be permeable or impermeable to blood and/or other fluids, such as water. In some embodiments, the membrane 230 may include a polymeric membrane, a metallic or polymeric mesh, a porous filter-like material, or other suitable construction. In some embodiments, the membrane 230 prevents thrombi (i.e. blood clots, etc.) from passing through the membrane 230 and out of the left atrial appendage into the blood stream. In some embodiments, the membrane 230 promotes endothelization after implantation, thereby effectively removing the left atrial appendage from the patient's circulatory system.

FIG. 12 illustrates a partial cross-sectional view of the implant 200 disposed within an example left atrial appendage, such as that shown in FIG. 2, in a deployed position. As can be seen in FIG. 12, the support frame 210 may be compliant and substantially conform to and/or be in sealing engagement with the shape and/or geometry of the lateral wall of the left atrial appendage in the deployed position. At its largest size, extent, or shape, the implant 200 may expand to the fourth, unconstrained position in the deployed position. In some embodiments, the implant 200 may expand to a size, extent, or shape less than or different from the fourth, unconstrained position in the deployed position, which may be partially constrained, as determined by the surrounding tissue and/or lateral wall of the left atrial appendage. Reducing the thickness of the plurality of struts compared to the device shown in FIG. 3 increases the flexibility and compliance of the support frame 210 and/or the implant 200, thereby permitting the implant 200 to conform to the tissue around it, rather than forcing the tissue to conform to the implant.

In some embodiments, the plurality of struts of the support frame 210 and/or the plurality of anchors 250 may be formed of or include a metallic material, a metallic alloy, a ceramic material, a rigid or high performance polymer, a metallic-polymer composite, combinations thereof, and the like. Some examples of some suitable materials may include metallic materials and/or alloys such as stainless steel (e.g., 303, 304v, or 316L stainless steel), nickel-titanium alloy (e.g., nitinol, such as super elastic or linear elastic nitinol), nickel-chromium alloy, nickel-chromium-iron alloy, cobalt alloy, nickel, titanium, platinum, or alternatively, a polymer material, such as a high performance polymer, or other suitable materials, and the like. The word nitinol was coined by a group of researchers at the United States Naval Ordinance Laboratory (NOL) who were the first to observe the shape memory behavior of this material. The word nitinol is an acronym including the chemical symbol for nickel (Ni), the chemical symbol for titanium (Ti), and an acronym identifying the Naval Ordinance Laboratory (NOL).

In some embodiments, the plurality of struts of the support frame 210 and/or the plurality of anchors 250 may be mixed with, may be doped with, may be coated with, or may otherwise include a radiopaque material. Radiopaque materials are understood to be materials capable of producing a relatively bright image on a fluoroscopy screen or another imaging technique such as X-ray during a medical procedure. This relatively bright image aids the user of device in determining its location. Suitable radiopaque materials may include, but are not limited to, bismuth subcarbonate, iodine, gold, platinum, palladium, tantalum, tungsten or tungsten alloy, and the like.

In some embodiments, the membrane 230 may be formed of or include a polymeric material, a metallic or metallic alloy material, a metallic-polymer composite, combinations thereof, and the like. In some embodiments, the membrane 230 is preferably formed of polyethylene terephthalate (PET) such as DACRON®, or expanded polytetrafluoroethylene (ePTFE). Other examples of suitable polymers may include polyurethane, a polyether-ester such as ARNITEL® available from DSM Engineering Plastics, a polyester such as HYTREL® available from DuPont, a linear low density polyethylene such as REXELL®, a polyamide such as DURETHAN® available from Bayer or CRISTAMID® available from Elf Atochem, an elastomeric polyamide, a block polyamide/ether, a polyether block amide such as PEBA available under the trade name PEBAX®, silicones, polyethylene, Marlex high-density polyethylene, polytetrafluoroethylene (PTFE), polyetheretherketone (PEEK), polyimide (PI), and polyetherimide (PEI), a liquid crystal polymer (LCP) alone or blended with other materials.

In some embodiments, the delivery catheter 290 and/or the implant 200 may be made from, may be mixed with, may be coated with, or may otherwise include a material that provides a smooth, slick outer surface. In some embodiments, the delivery catheter 290 and/or the implant 200 may include or be coated with a lubricious coating, a hydrophilic coating, a hydrophobic coating, a drug-eluting material, an anti-thrombus coating, or other suitable coating depending on the intended use or application.

It should be understood that although the above discussion was focused on a medical device and methods of use within the vascular system of a patient, other embodiments of medical devices or methods in accordance with the disclosure can be adapted and configured for use in other parts of the anatomy of a patient. For example, devices and methods in accordance with the disclosure can be adapted for use in the digestive or gastrointestinal tract, such as in the mouth, throat, small and large intestine, colon, rectum, and the like. For another example, devices and methods can be adapted and configured for use within the respiratory tract, such as in the mouth, nose, throat, bronchial passages, nasal passages, lungs, and the like. Similarly, the apparatus and/or medical devices described herein with respect to percutaneous deployment may be used in other types of surgical procedures as appropriate. For example, in some embodiments, the medical devices may be deployed in a non-percutaneous procedure, such as an open heart procedure. Devices and methods in accordance with the invention can also be adapted and configured for other uses within the anatomy.

It should be understood that this disclosure is, in many respects, only illustrative. Changes may be made in details, particularly in matters of shape, size, and arrangement of steps without exceeding the scope of the invention. The invention's scope is, of course, defined in the language in which the appended claims are expressed.

What is claimed:

1. A medical device for left atrial appendage closure, comprising:
 a monolithic support frame formed from a plurality of struts extending continuously between a proximal collar and a distal collar, wherein the monolithic support frame includes a longitudinal axis extending between the proximal collar and the distal collar;
 wherein the plurality of struts includes a first grouping of cells adjacent to the proximal collar and defining a first row, a second grouping of cells defining a second row adjacent to the first row, a third grouping of cells defining a third row adjacent to the second row, a fourth grouping of cells defining a fourth row adjacent to the third row and a fifth grouping of cells adjacent to the distal collar and defining a fifth row adjacent to the fourth row;
 wherein the monolithic support frame extends distally and curves away from the proximal collar along a first bend, and wherein the monolithic support frame extends radially away from the first bend to a second bend, and wherein the monolithic support frame extends distally and curves radially inward along the second bend;
 wherein the monolithic support frame extends from the second bend to a third bend along a first segment, and wherein a first angle is defined between the first segment and a reference axis parallel to the central axis, and wherein the first angle is between 5 and 25 degrees;
 wherein the monolithic support frame extends from the third bend along a second segment, and wherein a second angle is defined between the first segment and the second segment, and wherein the second angle is between 20 and 65 degrees.

2. The medical device of claim 1, wherein the first row includes at least one diamond-shaped cell.

3. The medical device of claim 1, wherein the width of at least one cell of the second grouping of cells is different than the width of the cells defining the first grouping of cells.

4. The medical device of claim 3, wherein the width of at least one cell of the second grouping of cells is wider than the width of the cells defining the first grouping of cells.

5. The medical device of claim 4, wherein the width of at least one cell of the third grouping of cells is different than the width of the cells defining the second grouping of cells.

6. The medical device of claim 5, wherein the width of at least one cell of the third grouping of cells is wider than the width of the cells defining the second grouping of cells.

7. The medical device of claim 1, wherein the proximal collar and the distal collar together define a longitudinal axis and wherein the struts defining the first grouping of cells are fixedly attached to the proximal collar and initially extend distally from the proximal collar.

8. The medical device of claim 7, wherein the struts defining the fifth grouping of cells are fixedly attached to the distal collar and initially extend distally from the distal collar.

9. The medical device of claim 1, wherein the plurality of struts extending between the proximal collar and the distal collar and define an interior volume of the support frame, and wherein the proximal collar is located outside the interior volume of the support frame and the distal collar is located within the interior volume of the support frame.

10. The medical device of claim 1, wherein the support frame is configured to shift between a first unexpanded configuration and an expanded configuration, and wherein when in the expanded configuration, the distal collar is positioned proximal of a distalmost extent of the support frame.

11. The medical device of claim 1, further comprising a plurality of anchors formed integrally with the support frame.

12. The medical device of claim 1, further comprising a membrane disposed over at least a portion of the support frame.

13. A left atrial appendage closure system, comprising:
 a delivery catheter;
 a delivery shaft slidably disposed within the lumen of the delivery catheter, the delivery shaft having a distal end releasably attached to a proximal collar of a monolithic support frame, wherein the monolithic support frame is formed from a plurality of struts extending continuously between the proximal collar and a distal collar, wherein the monolithic support frame includes a longitudinal axis extending between the proximal collar and the distal collar, and wherein the plurality of struts includes a first grouping of cells adjacent to the proximal collar and defining a first row, a second grouping of cells defining a second row adjacent to the first row, a third grouping of cells defining a third row adjacent to the second row, a fourth grouping of cells defining a fourth row adjacent to the third row and a fifth grouping of cells adjacent to the distal collar and defining a fifth row adjacent to the fourth row,
 wherein the monolithic support frame extends distally and curves away from the proximal collar along a first bend, and wherein the monolithic support frame extends radially away from the first bend to a second bend, and wherein the monolithic support frame extends distally and curves radially inward along the second bend;
 wherein the monolithic support frame extends from the second bend to a third bend along a first segment, and wherein a first angle is defined between the first segment and a reference axis parallel to the central axis, and wherein the first angle is between 5 and 25 degrees;
 wherein the monolithic support frame extends from the third bend along a second segment, and wherein a second angle is defined between the first segment and the second segment, and wherein the second angle is between 20 and 65 degrees.

14. The medical device of claim 13, further comprising a plurality of anchors formed integrally with the support frame.

15

16

15. The medical device of claim 14, further comprising a membrane disposed over at least a portion of the support frame.

16. The medical device of claim 13, wherein the first row includes at least one diamond-shaped cell.

17. The medical device of claim 16, wherein the width of at least one cell of the second grouping of cells is different than the width of the cells defining the first grouping of cells.

18. The medical device of claim 17, wherein the width of at least one cell of the second grouping of cells is wider than the width of the cells defining the first grouping of cells.

19. The medical device of claim 18, wherein the width of at least one cell of the third grouping of cells is different than the width of the cells defining the second grouping of cells.

20. A method of occluding a left atrial appendage, the method including:

positioning a left atrial appendage occlusion device adjacent a left atrial appendage, the left atrial appendage device including:

a monolithic support frame formed from a plurality of struts extending continuously between a proximal collar and a distal collar, wherein the monolithic support frame includes a longitudinal axis extending between the proximal collar and the distal collar;

wherein the plurality of struts includes a first grouping of cells adjacent to the proximal collar and defining a first row, a second grouping of cells defining a second row adjacent to the first row, a third grouping of cells defining a third row adjacent to the second row, a fourth grouping of cells defining a fourth row adjacent to the third row and a fifth grouping of cells adjacent to the distal collar and defining a fifth row adjacent to the fourth row;

wherein the monolithic support frame extends distally and curves away from the proximal collar along a first bend, and wherein the monolithic support frame extends radially away from the first bend to a second bend, and wherein the monolithic support frame extends distally and curves radially inward along the second bend;

wherein the monolithic support frame extends from the second bend to a third bend along a first segment, and wherein a first angle is defined between the first segment and a reference axis parallel to the central axis, and wherein the first angle is between 5 and 25 degrees;

wherein the monolithic support frame extends from the third bend along a second segment, and wherein a second angle is defined between the first segment and the second segment, and wherein the second angle is between 20 and 65 degrees; and expanding the left atrial appendage occlusion device within the left atrial appendage.

* * * * *